United States Patent
Rodriguez

(10) Patent No.: US 6,541,410 B1
(45) Date of Patent: Apr. 1, 2003

(54) SILOXY SUBSTITUTED COCATALYST ACTIVATORS FOR OLEFIN POLYMERIZATION

(75) Inventor: George Rodriguez, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/599,909

(22) Filed: Jun. 23, 2000

(51) Int. Cl.⁷ .............. B01J 31/00; B01J 37/00; C08F 4/02; C08F 4/60; C08F 4/44
(52) U.S. Cl. .............. 502/103; 502/117; 502/152; 502/155; 502/158; 526/134; 526/160; 526/943
(58) Field of Search .................. 502/103, 152, 502/155, 158, 117; 526/134, 160, 943

(56) References Cited

U.S. PATENT DOCUMENTS

| | | | |
|---|---|---|---|
| 5,198,401 A | | 3/1993 | Turner et al. |
| 5,278,119 A | | 1/1994 | Turner et al. |
| 5,332,706 A | * | 7/1994 | Nowlin et al. .......... 502/117 |
| 5,502,017 A | * | 3/1996 | Marks et al. .......... 502/117 |
| 5,846,895 A | * | 12/1998 | Gila et al. .......... 502/117 |
| 5,972,823 A | * | 10/1999 | Walzer, Jr. .......... 502/152 |
| 6,060,418 A | * | 5/2000 | Sangokoya .......... 502/117 |
| 6,087,293 A | * | 7/2000 | Carnahan et al. .......... 502/155 |
| 6,114,555 A | * | 9/2000 | Llinas et al. .......... 502/103 |
| 6,133,187 A | * | 10/2000 | Vega et al. .......... 502/103 |
| 6,156,690 A | * | 12/2000 | Hosaka .......... 502/103 |
| 6,187,940 B1 | * | 2/2001 | Chen et al. .......... 502/103 |
| 6,200,921 B1 | * | 3/2001 | Kataoka .......... 502/103 |
| 6,214,760 B1 | * | 4/2001 | Chen et al. .......... 502/103 |
| 6,232,261 B1 | * | 5/2001 | Little .......... 502/152 |
| 6,248,914 B1 | * | 6/2001 | Klosin .......... 502/103 |

FOREIGN PATENT DOCUMENTS

| | | |
|---|---|---|
| EP | 0 277 003 A | 3/1988 |
| EP | 0 277 004 A | 3/1988 |
| WO | WO 96/28480 | 9/1996 |
| WO | WO 97/19959 | 6/1997 |

OTHER PUBLICATIONS

"$\eta^5$–$C_5Me_5TiMe_3B(C_6F_5)_3$: A Carbocationic Olefin Polymerization Initiator Masquerading As A Ziegler–Natta Catalyst," Michael C. Baird, et al, J. Am. Chem. Soc., vol. 116, p. 6435–6435 (1994).

"The Search For Larger And More Weakly Coordinating Anions," Steven H. Strauss, Chem. Rev., vol. 93, p. 927–942 (1993).

* cited by examiner

Primary Examiner—Mark L. Bell
Assistant Examiner—J. Pasterczyk
(74) Attorney, Agent, or Firm—Charles E. Runyan

(57) ABSTRACT

This description addresses ionic compositions of matter comprising positively charged cations [Ct]⁺ and negatively charged anions [A]⁻, said anion comprising a central core Group 13 element to which are bound fluoroaryl ligands, at least one of said fluoroaryl ligands being substituted with a siloxy group represented by the symbols—$SiOR_3$, wherein R is a $C_1$–$C_{30}$ hydrocarbyl or hydrocarbylsilyl substituent. [Ct]⁺ may be selected from any capable of use with olefin polymerization catalysts and typically will be from the group consisting of anilinium and ammonium cations, trityl carbenium cations, Group 11 metal cations, silylium cations, the cations of the hydrated salts of Group 1 or 2 metals, and derivatives of the foregoing anilinium, ammonium, trityl carbenium, and silylium cations containing $C_1$–$C_{20}$ hydrocarbyl, hydrocarbylsilyl, or hydrocarbylamine substituents for one or more hydrogen atoms of said cations. The ionic compositions described can be used to activate olefin polymerization catalysts, and can be prepared so as to be soluble in aliphatic solvents. Syntheses and polymerization are illustrated.

27 Claims, No Drawings

SILOXY SUBSTITUTED COCATALYST ACTIVATORS FOR OLEFIN POLYMERIZATION

TECHNICAL FIELD

This invention relates to polymerization cocatalyst compounds containing weakly coordinating Group 13 element anions and to the preparation of olefin polymers using ionic catalyst systems based on organometallic transition metal cationic compounds stabilized by these anions.

BACKGROUND ART

The term "noncoordinating anion" is now accepted terminology in the field of olefin and vinyl monomer polymerization, both by coordination or insertion polymerization and carbocationic polymerization. See, for example, EP 0 277 003, EP 0 277 004, U.S. Pat. Nos. 5,198,401, 5,278,119, and Baird, Michael C., et al, J. Am. Chem. Soc. 1994, 116, 6435–6436. The noncoordinating anions are described to function as electronic stabilizing cocatalysts, or counterions, for essentially cationic metallocene complexes which are active for polymerization. The term noncoordinating anion as used here applies both to truly noncoordinating anions and coordinating anions that are at most weakly coordinated to the cationic complex so as to be labile to replacement by olefinically or acetylenically unsaturated monomers at the insertion site. These noncoordinating anions can be effectively introduced into a polymerization medium, or premixed with an organometallic catalyst compound prior to introduction into the polymerization medium, as Bronsted acid salts containing charge-balancing countercations, ionic cocatalyst compounds. See also, the review articles by S. H. Strauss, "The Search for Larger and More Weakly Coordinating Anions", Chem. Rev., 93, 927–942 (1993).

Olefin solution polymerization processes are generally conducted in aliphatic solvents that serve both to maintain reaction medium temperature profiles and solvate the polymer products prepared. However, aryl-group containing activators, such as those having phenyl derivatives and other fused or pendant aryl-group substituents, are at best sparingly soluble in such solvents and typically are introduced in aryl solvents such as toluene. Solution polymerization processes in aliphatic solvents thus can be contaminated with toluene that must be removed to maintain process efficiencies and to accommodate health-related concerns for both industrial manufacturing processes and polymer products from them. Alternatively, relatively insoluble catalyst components can be introduced via slurry methods, but such methods required specialized handling and pumping procedures that complicate and add significant costs to industrial scale plant design and operation. Low solubility can also become disadvantageous should the process involve low temperature operation at some stage such as in typical adiabatic processes run in areas subject to low ambient temperatures. Additionally, separating or counteracting the build up in the recycle system of aromatic catalyst solvents may become another problem. At the same time means of maintaining high molecular weights in olefin polymers while operating at economically preferable high polymerization reaction temperatures and high polymer production rates is highly desirable. It is therefore desirable to identify olefin polymerization cocatalyst activators which are active for polymerization, particularly at elevated temperatures, which are more soluble in aliphatic solvents.

U.S. Pat. No. 5,502,017 addresses ionic metallocene catalysts for olefin polymerization comprising, as a cocatalyst component, a weakly coordinating anion comprising boron substituted with halogenated aryl substituents preferably containing silylalkyl substitution, such as tert-butyldimethyl-silyl. This substitution is said to increase the solubility and thermal stability of the resulting metallocene salts. Examples 3–5 describes the synthesis and polymerization use of the cocatalyst compound triphenylcarbenium tetrakis(4-dimethyl-t-butylsilyl-2,3,5,6-tetrafluorophenyl) borate.

In view of the above there is a continuing need for activating cocatalyst compounds both to improve the industrial economics of solution polymerization and to provide alternative activating compounds for ionic, olefin polymerization catalyst systems.

BRIEF SUMMARY OF THE INVENTION

The invention provides anion-containing cocatalyst precursor compounds which can be combined with organometallic catalyst precursor compounds to form active catalysts for olefin polymerization by insertion, or coordination, and by carbocationic methods. Olefin polymerization can be conducted by subsequent contacting, or in situ catalyst formation essentially concurrent with said contacting, with polymerizable monomers, those having accessible olefinic, acetylenic unsaturation, or with monomers having olefinic unsaturation capable of cationic polymerization. The catalysts according to the invention are suitable for preparing polymers and copolymers from olefinically and acetylenically unsaturated monomers. The anions [A]⁻ of the cocatalyst precursor compounds are those containing a central Group 13 core element to which are bound fluoroaryl ligands, at least one of said fluoroaryl ligands being substituted in the para-position with a siloxy group represented by the symbol, —OSiR$_3$, R representing one or more alkyl or alkylsilyl groups. When the anions are to be used with anilinium or ammonium cations, R groups are secondary, or even tertiary alkyl or alkylsilyl groups when capable of use in view of steric hindrance problems.

Preferred invention cocatalyst activator compounds can be represented by the following formula:

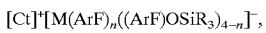

[Ct]⁺[M(ArF)$_n$((ArF)OSiR$_3$)$_{4-n}$]⁻, where [Ct]⁺ is a cation capable of abstracting an alkyl group, or breaking a carbon-metal bond from organometallic compounds containing such, M is a Group 13 element, preferably boron or aluminum, ArF is a fluorinated aryl group, and each R is independently selected from C$_1$–C$_{30}$ hydrocarbyl or hydrocarbylsilyl substituents, preferably attached to the Si atom through a secondary or tertiary carbon atom.

DETAILED DESCRIPTION OF THE INVENTION

Exemplary ArF ligands and substituents of the above invention specifically include fluorinated aryl groups, preferably perfluorinated aryl groups, and include substituted ArF groups having substituents additional to the fluorine substitution, such as fluorinated hydrocarbyl groups. Preferred fluorinated aryl groups include phenyl, biphenyl, napthyl and derivatives thereof. The disclosures of U.S. Pat. Nos. 5,198,401, 5,296,433, 5,278,119, 5,447,895, 5,688, 634, 5,895,771, WO 93/02099, WO 97/29845, WO 99/43717, WO 99/42467 and copending U.S. application Ser. No. 09/261,627, filed Mar. 3, 1999, and its equivalent WO 99/45042 are particularly instructive as to suitable ArF chemical groups and are incorporated by reference for purposes of U.S. patent practice. It is preferred that at least one third of hydrogen atoms on carbon atoms of the aromatic ligands be replaced by fluorine atoms, and more preferred that the aryl ligands be perfluorinated ligands. Perfluorinated means that each aryl hydrogen atom, other than those substituted with the siloxy substituents of the invention, should be substituted with fluorine or fluorcarbyl substituents, e.g., trifluoromethyl. The term "perfluorinated" also encompasses those aryl ligands in which all but one hydrogen atom in the para position is replaced with fluorine and the para-position hydrogen is replaced with a siloxy group according to the invention.

Essentially any of the defined R groups will be effective for olefin polymerization such as by solution, bulk, slurry and gas phase polymerization processes. Exemplary R groups include methyl, ethyl, n-propyl, iso-propyl, n-butyl, tert-butyl, cyclohexyl, benzyl, methyltrimethylsilyl, methyltriethylsilyl, etc. The R groups may be the same or different, in other words mixed alkyl groups may be located on the siloxy silicon atom. In one embodiment, each R is a $C_{1-20}$ hydrocarbyl or hydrocarbylsilyl substituent, preferably attached to the Si of the —O—Si— group through a secondary or tertiary carbon atom. Tertiary-carbon containing substituents can be advantageously employed where the two other R groups are less bulky, that is lower alkyl ($C_1$–$C_4$) primary or secondary alkyl substituents so as to minimize steric hindrance problems. Particular advantage in solution polymerization can be realized by selecting R such that solubility in aliphatic solvents is effectively achieved. The term "effective solubility", and equivalent phraseology, is used here to mean having sufficient solubility such that amounts of cocatalyst reagent dissolved in an aliphatic solvent such as hexane are capable of activating industrially useful amounts of organometallic catalyst compounds without the use of aromatic solvents or slurry techniques. For example the selection of $C_2$, or higher carbon-number alkyl or silylalkyl groups on the silicon atom, provides effective solubility.

Effective cations ($Ct^+$) can be any of those known to be suitable for the abstraction of any of monoanionic hydride, alkyl, or other hydrocarbyl or hydrocarbylsilyl ligands on organometallic compounds suitable as insertion polymerization catalysis, or scission of covalent metal-carbon $\eta^1$ or $\eta^2$ bonds in such organometallic compounds. Preferably the cation is essentially non-interfering with the ionic catalyst complexes formed with the organometal catalyst precursor compounds. Such include nitrogen-containing cations such as the anilinium and ammonium salts of U.S. Pat. No. 5,198,401, and WO 97/35893, the trityl carbenium cations of U.S. Pat. No. 5,387,568, metal cations, e.g., $Ag^+$, the silylium cations of WO 96/08519, and the cations of the hydrated salts of Group 1 or 2 metals of U.S. Pat. No. 5,767,208. Additionally suitable cations include nitrogen and carbon based cations described in WO 97/35893, and in copending U.S. applications serial No. 60/160,942, filed Oct. 22, 1999, and No. 60/169,768, filed Dec. 9, 1999. Thus hydrocarbyl, hydrocarbyl-amine, hydrocarbyl-silyl, preferably $C_1$–$C_{20}$, and Group 1, 2, 11 and 12 metal based cations, are suitable in accordance with the invention. An example of a hydrocarbyl-amine is [N-pentafluorophenyl pyrrolidinium]. The teachings of these references are referred to for information and incorporated by reference for the purposes of U.S. patent practice.

The ionic activator cocatalyst compositions of the invention may be prepared by synthetic methods well within the skills of organic and organometallic chemists. In a typical procedure, bromo-tetrafluorophenol is converted to the siloxy substituted counterpart by reacting with a trialkylchlorosilane in the presence of a strong base such as potassium hydride. The reaction product is then converted by reaction with BuLi and appropriate amount of a trihalylborane or aluminane. The resulting lithium salt can then be converted to an activating cocatalyst salt by cation exchange reaction with a halide salt, for example aninilinium or ammonium salts. This reaction sequence is illustrated below.

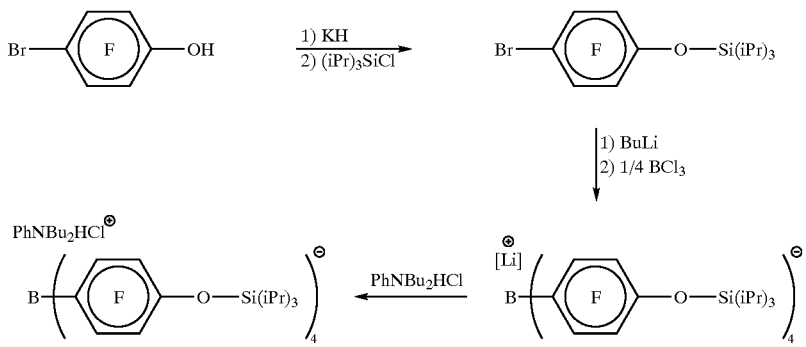

Organometallic precursors compounds suitable as olefin polymerization catalysts by coordination or insertion polymerization in accordance with the invention will include the known organometallic, transition metal compounds useful in traditional Ziegler-Natta coordination polymerization, particularly the metallocene compounds known to be useful in coordination polymerization, when such compounds are capable of catalytic activation by the cocatalyst activators described for the invention. These will typically include Group 3–10 transition metal compounds wherein at least one metal ligand can be abstracted by the cocatalyst activators, particularly those ligands including hydride, hydrocarbyl, and hydrocarbylsilyl, and lower alkyl-substituted ($C_1$–$C_{10}$) derivatives of those. Examples include hydride, methyl, benzyl, dimethyl-butadiene, etc. Ligands capable of being abstracted and transition metal compounds comprising them include those metallocenes described in the background art, see for example U.S. Pat. No. 5,198,401 and WO 92/00333. Syntheses of these compounds is well known from the published literature. Additionally, where the metal ligands include halogen, amido or alkoxy labile ligands (for example, biscyclopentadienyl zirconium dichloride) which not allow for ready abstraction with the activating cocatalysts of the invention, they can be converted into suitable ligands via known alkylation reactions with organometallic compounds such as lithium or aluminum hydrides or alkyls, alkylalumoxanes, Grignard reagents, etc. See also EP 0 500 944 and EP 0 570 982 for the reaction of organoaluminum compounds with dihalo-substituted . metallocene compounds prior to addition of activating anion compounds. All documents are incorporated by reference for purposes of U.S. patent practice.

Additional description of metallocene compounds which comprise, or can be alkylated to comprise, at least one ligand capable of abstraction to form a catalyticly active transition metal cation appear in the patent literature, e.g., EP-A-0 129 368, U.S. Pat. Nos. 4,871,705, 4,937,299, 5,324,800, 5,470, 993, 5,491,246, 5,512,693, EP-A-0 418 044, EP-A-0 591 756, WO-A-92/00333, WO-A-94/01471 and WO 97/22635. Such metallocene compounds can be described for this invention as mono- or biscyclopentadienyl substituted Group 3, 4, 5, or 6 transition metal compounds wherein the ancillary ligands may be themselves substituted with one or more groups and may be bridged to each other, or may be bridged through a heteroatom to the transition metal. The size and constituency of the ancillary ligands and bridging elements are not critical to the preparation of the ionic catalyst systems of the invention but should be selected in the literature described manner to enhance the polymerization activity and polymer characteristics being sought. Preferably the cyclopentadienyl rings (including substituted cyclopentadienyl-based fused ring systems, such as indenyl, fluorenyl, azulenyl, or substituted analogs of them), when bridged to each other, will be lower alkyl-substituted ($C_1$–$C_6$) in the 2 position (without or without a similar 4-position substituent in the fused ring systems) and may additionally comprise alkyl, cycloalkyl, aryl, alkylaryl and or arylalkyl substituents, the latter as linear, branched or cyclic structures including multi-ring structures, for example, those of U.S. Pat. Nos. 5,278,264 and 5,304,614. Such substituents should each have essentially hydrocarbyl characteristics and will typically contain up to 30 carbon atoms but may be heteroatom containing with 1–5 non-hydrogen/carbon atoms, e.g., N, S, O, P, Ge, B and Si. All documents are incorporated by reference for purposes of U.S. patent practice.

Metallocene compounds suitable for the preparation of linear polyethylene or ethylene-containing copolymers (where copolymer means comprising at least two different monomers) are essentially any of those known in the art, see again WO-A-92/00333 and U.S. Pat. Nos. 5,001,205, 5,198, 401, 5,324,800, 5,304,614 and 5,308,816, for specific listings. Selection of metallocene compounds for use to make isotactic or syndiotactic polypropylene, and their syntheses, are well-known in the art, specific reference may be made to both patent literature and academic, see for example Journal of organometallic Chemistry 369, 359–370 (1989). Typically those catalysts are stereorigid asymmetric, chiral or bridged chiral metallocenes. See, for example, U.S. Pat. Nos. 4,892,851, 5,017,714, 5,296,434, 5,278,264, WO-A-(PCT/US92/10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, Organometallics 1994, 13, 954–963, and "ansa-Zirconocene Polymerization Catalysts with Annelated Ring Ligands-Effects on Catalytic Activity and Polymer Chain Lengths", Brinzinger, H., et al, Organometallics 1994, 13, 964–970, and documents referred to therein. Though many above are directed to catalyst systems with alumoxane activators, the analogous metallocene compounds will be useful with the cocatalyst activators of this invention for active coordination catalyst systems, when the halogen, amide or alkoxy containing ligands of the metals (where occurring) are replaced with ligands capable of abstraction, for example, via an alkylation reaction as described above, and another is a group into which the ethylene group —C=C— may insert, for example, hydride, alkyl, alkenyl, or silyl. See additional description in G. G. Hlatky, "Metallocene catalysts for olefin polymerization Annual review of 1996", Coordination Chemistry Reviews, 181, 243–296 (Elsevier Science, 1999). All documents are incorporated by reference for purposes of U.S. patent practice.

Representative metallocene compounds can have the formula:

$$L^A L^B L^C_i McDE$$

where, Mc is a Group 3–6 metal; $L^A$ is a substituted or unsubstituted cyclopentadienyl or heterocyclopentadienyl ancillary ligand π-bonded to Mc; $L^B$ is a member of the class of ancillary ligands defined for $L_A$, or is J, a heteroatom ancillary ligand σ-bonded to Mc; the $L^A$ and $L^B$ ligands may be covalently bridged together through one or more Group 13–16 element-containing linking groups; $L^C_i$ is an optional neutral, non-oxidizing ligand having a dative bond to Mc (i equals 0 to 3); and, D and E are independently labile ligands, each having a metal-carbon bond to Mc, optionally bridged to each other or $L^A$ or $L^B$, which bond can be broken for abstraction purposes by a suitable activator and into which a polymerizable monomer or macromonomer can insert for coordination polymerization. Also, the use of hetero-atom containing rings or fused rings, where a non-carbon Group 13, 14, 15 or 16 atom replaces one of the ring carbons is considered for this specification to be within the terms "cyclopentadienyl", "indenyl", and "fluorenyl". See, for example, the background and teachings of WO 98/37106, having common priority with U.S. Ser. No. 08/999,214, filed Dec. 29, 1997, and WO 98/41530, having common priority with U.S. Ser. No. 09/042,378, filed Mar. 13, 1998, both incorporated by reference for purposes of U.S. patent practice. Substituted cyclopentadienyl structures means that one or more hydrogen atoms is replaced with hydrocarbyl, hydrocarbylsilyl, or heteroatom-containing like structures. The hydrocarbyl structures specifically include $C_1$–$C_{30}$ linear, branched, cyclic alkyl and cycloaromatic fused and pendent rings. These rings may also be substituted with similar structures.

Non-limiting representative metallocene compounds include monocyclopentadienyl compounds such as pentamethylcyclopentadienyltitanium isopropoxide, pentamethylcyclopentadienyltribenzyl titanium, dimethylsilyltetramethylcyclopentadienyl-tert-butylamido titanium dichloride, pentamethylcyclopentadienyl titanium trimethyl, dimethylsilyltetramethylcyclopentadienyl-tert-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis(1,3-butyl, methylcyclopentadienyl) zirconium dimethyl, pentamethylcyclopentadienyl-cyclopentadienyl zirconium dimethyl, (tetramethylcyclopentadienyl)(n-propylcyclopentadienyl) zirconium dimethyl; bridged bis-cyclopentadienyl compounds such as dimethylsilylbis(tetrahydroindenyl) zirconium dichloride and silacyclobutyl (tetramethylcyclopentadienyl)(n-propyl-cyclopentadienyl) zirconium dimethyl; bridged bisindenyl compounds such as dimethylsilylbisindenyl zirconium dichloride, dimethylsilylbisindenyl hafnium dimethyl, dimethylsilylbis(2-methylbenzindenyl)zirconium dichloride, dimethylsilylbis (2-methylbenzindenyl)zirconium dimethyl; and fluorenyl ligand-containing compounds, e.g., diphenylmethyl (fluorenyl)(cyclopentadienyl)zirconium dimethyl; and the additional mono- and biscyclopentadienyl compounds such as those listed and described in U.S. Pat. Nos. 5,017,714, 5,324,800, WO 92/00333 and EP-A-0 591 756. Particular advantage in solution polymerization can be achieved by the use of aliphatic solvent-soluble precursor compounds, e.g., bis(para-triethylsilyl-phenyl)methylene (2,7-(di-tert-butyl) fluorenyl)(cyclopentadienyl)hafnium dimethyl, however, the solubilizing effect of the aliphatic solvent-soluble anion compounds of the invention will tend to offset the lack of solubility for typical organometallic compound cations useful in olefin polymerization. See, copending applications U.S. Ser. No. 09/426,099, filed Oct. 22, 1999, and No. 60/160,942, filed Oct. 22, 1999 for background as to soluble catalysts and specific metallocene and precursor cocatalyst cations useful with the current invention. All documents are incorporated by reference for purposes of U.S. patent practice.

Representative traditional Ziegler-Natta transition metal compounds include tetrabenzyl zirconium, tetra bis (trimethylsiylmethyl)zirconium, oxotris (trimethlsilylmethyl)vanadium, tetrabenzyl hafnium, tetrabenzyl titanium, bis(hexamethyldisilazido)dimethyl titanium, tris(trimethylsilylmethyl)niobium dichloride, tris (trimethylsilylmethyl)tantalum dichloride. The important features of such compositions for coordination polymerization are the ligand capable of abstraction and that ligand into which the ethylene (olefinic) group can be inserted. These features enable the ligand abstraction from the transition metal compound and the concomitant formation of the ionic catalyst composition of the invention.

Additional organometallic transition metal compounds suitable as olefin polymerization catalysts in accordance with the invention will be any of those Group 3–10 that can be converted by ligand abstraction or σ-bond scission into a catalyticly active cation and stabilized in that active electronic state by a noncoordinating or weakly coordinating anion sufficiently labile to be displaced by an olefinically unsaturated monomer such as ethylene.

Exemplary compounds include those described in the patent literature. International patent publications WO 96/23010, WO 97/48735 and Gibson, et. al., Chem. Comm., pp. 849–850 (1998), disclose diimine-based ligands for Group 8–10 metal compounds shown to be suitable for ionic activation and olefin polymerization. See also WO 97/48735. Transition metal polymerization catalyst systems from Group 5–10 metals wherein the active transition metal center is in a high oxidation state and stabilized by low coordination number polyanionic ancillary ligand systems are described in U.S. Pat. No. 5,502,124 and its divisional U.S. Pat. No. 5,504,049. See also the Group 5 organometallic catalyst compounds of U.S. Pat. No. 5,851,945 and the tridentate ligand containing Group 5–10 organometallic catalyst compounds of copending U.S. application Ser. No. 09/302,243, filed Apr. 29, 1999, and its equivalent PCT/US99/09306. Group 11 catalyst precursor compounds, capable of activation with ionizing cocatalysts, useful for olefins and vinyl group-containing polar monomers are described and exemplified in WO 99/30822 and its priority document, including U.S. patent application Ser. No. 08/991,160, filed Dec. 16, 1997. Each of these documents is incorporated by reference for the purposes of U.S. patent practice.

U.S. Pat. No. 5,318,935 describes bridged and unbridged bisamido transition metal catalyst compounds of Group 4 metals capable of insertion polymerization of α-olefins. Bridged bis(arylamido) Group 4 compounds for olefin polymerization are described by D. H. McConville, et al, in Organometallics 1995, 14, 5478–5480. Synthesis methods and compound characterization are presented. Further work appearing in D. H. McConville, et al, Macromolecules 1996, 29, 5241–5243, described bridged bis(arylamido) Group 4 compounds that are active catalysts for polymerization of 1-hexene. Additional transition metal compounds suitable in accordance with the invention include those described in WO 96/40805. Cationic Group 3 or Lanthanide metal complexes for coordination polymerization of olefins is disclosed in copending U.S. application Ser. No. 09/408,050, filed Sep. 29, 1999, and its equivalent PCT/US99/22690. The precursor metal compounds are stabilized by a monoanionic bidentate ancillary ligand and two monoanionic ligands and are capable of activation with the ionic cocatalysts of the invention. Each of these documents is incorporated by reference for the purposes of U.S. patent practice.

Additional description of suitable organometallic or organometalloid catalyst precursor compounds may be found in the literature, any of such will be suitable where comprising, or where capable of alkylation to comprise, ligands capable of ionizing abstraction. See, for instance, V. C. Gibson, et al, "The Search for New-Generation Olefin Polymerization Catalysts: Life Beyond Metallocenes", *Angew. Chem. Int. Ed*, 38, 428–447 (1999).

When using the above catalysts of the invention, the total catalyst system will generally additionally comprise one or more organometallic compound scavenging agent. Such compounds as used in this application and its claims is meant to include those compounds effective for removing polar impurities from the reaction environment and for increasing catalyst activity. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors are used to activate the catalyst systems. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of organometallic compound will still normally be used in the polymerization process itself.

Typically these compounds will be organometallic compounds such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl aluminumoxane. Those compounds having bulky or $C_6$–$C_{20}$ linear hydrocarbyl substituents covalently bound to the metal or metalloid center being preferred to minimize adverse interaction with the active catalyst. Examples include triethylaluminum, but more preferably, bulky compounds such as triisobutylaluminum, triusoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present can act as a poison scavenger compound and additional organometallic compounds may not be necessary. Alumoxanes also may be used in scavenging amounts with other means of activation, e.g., methylalumoxane and triisobutyl-aluminoxane with boron-based activators. The amount of such compounds to be used with catalyst compounds of the inventions is minimized during polymerization reactions to that amount effective to enhance activity (and with that amount necessary for activation of the catalyst compounds if used in a dual role) since excess amounts may act as catalyst poisons.

The catalyst compounds of the invention are useful in polymerization of unsaturated monomers conventionally known to be polymerizable under coordination polymerization using metallocenes. Such conditions are well known and include solution polymerization, slurry polymerization, gas-phase polymerization, and high pressure polymerization. The catalyst of the invention may be supported on inorganic oxide or polymeric supports and as such will be particularly useful in the known operating modes employing fixed-bed, moving-bed, fluid-bed, slurry or solution processes conducted in single, series or parallel reactors. Prepolymerization of supported catalyst of the invention may also be used for further control of polymer particle morphology in typical slurry or gas phase reaction processes in accordance with conventional teachings. A preferred method of supporting the invention catalysts for gas phase or slurry polymerization is described in WO 98/55518, incorporated by reference for purposes of U.S. patent practice.

In alternative embodiments of olefin polymerization methods for this invention, the catalyst system is employed in liquid phase (solution, slurry, suspension, bulk phase or combinations thereof), in high pressure liquid or supercritical fluid phase, or in gas phase. Each of these processes may also be employed in singular, parallel or series reactors. The liquid processes comprise contacting olefin monomers with the above described catalyst system in a suitable diluent or solvent and allowing said monomers to react for a sufficient time to produce the invention copolymers. Hydrocarbyl solvents are suitable, both aliphatic and aromatic, hexane is preferred. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5,352,749, 5,408,017, 5,436,304, 5,453,471, and 5,463,999, 5,767,208 and WO 95/07942. Each is incorporated by reference for purposes of U.S. patent practice.

Generally speaking, the polymerization reaction temperature can vary from about 40° C. to about 250° C. Preferably the polymerization reaction temperature will be from 60° C. to 220°. The pressure can vary from about 1 mm Hg to 2500 bar, preferably from 0.1 bar to 1600 bar, most preferably from 1.0 to 500 bar.

For homogenous solution polymerization best results may be obtained when the quantity and type of solvent used to introduce the catalyst is controlled as well as the manner of introduction. Generally it is believed preferable to achieve full solution and avoid slurried systems, and hence fairly high concentrations of the catalyst, at low temperatures and use low solvent amounts. The ease with which these objectives can be achieved may vary with the solubility of the non-coordinating anion and transition metal components. Some of the more active catalysts or those likely to give a higher molecular weight at a given temperature, may have reduced solubility or may be modified for increased solubility.

The invention is especially suitable for use with solution polymerization using bridged fluorenyl metallocene hafnium compounds with naphthyl group-containing non-coordinating anions at polymerization temperatures in excess of 110° C., for elastomeric olefin copolymers, and more preferably more than 160° C. and up to 250° C. for plastomeric ethylene copolymers.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, diolefins or cyclic olefins, are produced by adding ethylene, and optionally one or more of the other monomers, to a reaction vessel under low pressure (typically <50 bar), at a typical temperature of 40–250 ° C. with the invention catalyst that has been slurried with a solvent, such as hexane or toluene. Heat of polymerization is typically removed by cooling. Gas phase polymerization can be conducted, for example, in a continuous fluid bed gas-phase reactor operated at 2000–3000 kPa and 60–160 ° C., using hydrogen as a reaction modifier (100–200 PPM), $C_4$–$C_8$ comonomer feedstream (0.5–1.2 mol %), and $C_2$ feedstream (25–35 mol %). See, U.S. Pat. Nos. 4,543,399, 4,588,790, 5,028,670 and 5,405,922 and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between 40 and 160° C. The process can be carried out in a stirred tank reactor, or more than one operated in series or parallel. See the general disclosure of U.S. Pat. No. 5,001,205 for general process conditions. See also, international application WO 96/33227 and WO 97/22639. All documents are incorporated by reference for description of polymerization processes, metallocene selection and useful scavenging compounds.

Other olefinically unsaturated monomers besides those specifically described above may be polymerized using the catalysts according to the invention, for example, styrene, alkyl-substituted styrenes, isobutylene and other geminally disubstituted olefins, ethylidene norbornene, norbornadiene, dicyclopentadiene, and other olefinically-unsaturated monomers, including other cyclic olefins, such as cyclopentene, norbornene, alkyl-substituted norbornenes, and vinyl group-containing polar monomers capable of coordinating polymerization. See, for example, U.S. Pat. Nos. 5,635,573, 5,763,556, and WO 99/30822. Additionally, alpha-olefinic macromonomers of up to 1000 mer units, or more, may also be incorporated by copolymerization yielding branch-containing olefin polymers. Additionally oligomerization, dimerization, hydrogenation, olefin/carbon monoxide copolymerization, hydroformulation, hydrosilation, hydroamination and related catalytic reactions employing organometallic cationic complexes can be accomplished using the cocatalyst complexes of the invention with selected organometallic compounds suitably selected as known in the art.

The catalyst compositions of the invention can be used as described above individually for coordination polymerization or can be mixed to prepare polymer blends with other known olefin polymerization catalyst compounds. By selection of monomers, blends of coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

The formation of blended polymers can be achieved ex situ through mechanical blending or in situ through the use of a mixed catalyst system. It is generally believed that in situ blending provides a more homogeneous product and allows the blend to be produced in one step. The use of mixed catalyst systems for in situ blending involves combining more than one catalyst in the same reactor to simultaneously produce multiple distinct polymer products. This method requires additional catalyst synthesis and the various catalyst components must be matched for their activities, the polymer products they generate at specific conditions, and their response to changes in polymerization conditions.

EXAMPLES

The following examples are presented to illustrate the foregoing discussion. All parts, proportions and percentages are by weight unless otherwise indicated. All examples were carried out in dry, oxygen-free environments and solvents. Although the examples may be directed to certain embodiments of the present invention, they are not to be viewed as limiting the invention in any specific respect. In these examples certain abbreviations are used to facilitate the description. These include standard chemical abbreviations for the elements and certain commonly accepted abbreviations, such as Me=methyl, Et=ethyl, n-Pr=normal-propyl, t-Bu=tertiary-butyl, Ph=phenyl, pfp=pentafluorophenyl, Cp=cyclopentadienyl, Ind=indenyl, Flu=fluorenyl, TMS=trimethylsilyl, TES=triethylsilyl and THF (or thf)=tetrahydrofuran.

All molecular weights are weight average molecular weight unless otherwise noted. Molecular weights (weight average molecular weight (Mw) and number average molecular weight (Mn) were measured by Gel Permeation Chromatography (GPC) using a Waters 150 Gel Permeation Chromatograph equipped with a differential refractive index (DRI) and low angle light scattering (LS) detectors and calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.2 units for Mw/Mn which was calculated from elution times.

CATALYST PREPARATION

Example 1

Synthesis of $HC_6F_4OSi(iPr)_3$

To a tetrahydrofuran (thf) solution of 2,3,5,6-tetrafluorophenol (5 grams) was added one equivalent of potassium hydride as a suspension in thf The evolution of a gas was observed. After stirring for 1 hour, one equivalent of triisopropylchlorosilane was added. The reaction was allowed to stir for 16 hours. The solvent was replaced with pentane. The resulting precipitate byproduct was removed by filtration. The product was purified by column chromatography (silica gel, hexanes): yield=6.864 grams, 71%. $^1$H NMR (CDCl$_3$, 25° C.): δ6.65 (m, 1H), 1.29 (hp, 3H), 1.09 (d, 18H). $^{19}$F NMR (CDCl$_3$, 25° C.): δ−142.4 (m, 2F), −159.1 (m, 2F).

Example 2

Synthesis of $[Li(Et_2O)_{2.5}][B(C_6F_4OSi(iPr)_3)_4]$

To a cold diethyl ether solution of $HC_6F_4OSi(iPr)_3$ (6.864 grams) was added one equivalent of BuLi (1.6 M, hexane). After stirring for 1 hour, one quarter of an equivalent of boron trichloride was added. The solution was allowed to reach room temperature slowly, and stirred for 16 hours. The LiCl was remove by filtration. The volume of the filtrate was reduced to approximately 30% and pentane added to induce precipitation. The mixture was chilled at −35° C. for 16 hours and the product collected by filtration (B[C$_6$F$_4$OSi(iPr)$_3$]$_4$Li(Et$_2$O)$_{2.5}$): yield=6.804 grams, 86%. $^1$H NMR (CDCl$_3$, 25° C.): δ3.42 (q, 10H), 1.27 (hp, 12H), 1.15 (t,15H), 1.05 (d, 72H). $^{19}$F NMR (CDCl$_3$, 25° C.): δ−135.9 (m, 2F), −163.8 (m,2F).

Example 3

Synthesis of $[C_6H_5N(Bu)_2H][B(C_6F_4OSi(iPr)_3)_4]$

To a dichloromethane solution of (B[C$_6$F$_4$OSi(iPr)$_3$]$_4$Li (Et$_2$O)$_{2.5}$) (5.974 grams) was added one equivalent of C$_6$H$_5$N(Bu)$_2$HCl in dichloromethane. The reaction was stirred for 2 hours. The LiCl precipitate was collected by filtration and the solution volume reduced to approximately 30%. Pentane was added to induce precipitation. The mixture was chilled to −35° C. for 16 hours. The product collected by filtration was [C$_6$H$_5$N(Bu)$_2$H][B(C$_6$F$_4$OSi(iPr)$_3$)$_4$]: yield=5.488 grams, 91%. $^1$H NMR (Toluene-d$_8$, 25° C.): δ7.29 (t, 2H), 7.12 (t, 1H), 6.88 (d, 2H), 3.15 (4H), 1.36–0.80 (m, 98H). $^{19}$F NMR (Toluene-d$_8$, 25° C.): δ−129.6 (d, 8F), −157.0 (d, 8F).

POLYMERIZATION REACTIONS

Copolymerization of ethylene and propylene was carried out in a 2 litter, continuous stirred tank reactor operating at a reaction temperature of 100° C. using bis(para-triethylsilyl-phenyl)methylene(2,7-(di-tert-butyl)fluorenyl) (cyclopentadienyl)hafnium dimethyl as the metallocene catalyst. The compound of Example 3 was used as cocatalyst activator. Runs 1 and 2 of Tables 1a and 1b are representative. The catalyst system was preactivated in toluene for run 1. The catalyst system was preactivated in hexane for run 2. The collection times listed on Table 1 ("Time") refer to the time the polymer solutions were collected. A 25% (wt) solution of tri-n-octyl aluminium was used as an impurity scavenger. The scavenger to catalyst ratio for these two reactions were 17. The polymers were precipitated with isopropyl alcohol and dried in a vacuum oven at 75° C. The ethylene percentages in the samples were determined by IR (calibrated to NMR).

TABLE 1a

Copolymerization Reactions of Ethylene and Propylene.

| Run | Conc[1] % | Time[2] min | poly rate[3] g/hr | % C2 in EP | C2= feed g/hr | C3= feed g/hr | catalyst feed g/hr | C2= Conv[4] % | C3= Conv[4] % |
|---|---|---|---|---|---|---|---|---|---|
| 1 | 5.6 | 30 | 216 | 73.5 | 198 | 114 | 0.0145 | 80.3 | 50.3 |
| 2 | 5.7 | 30 | 219 | 73.5 | 198 | 114 | 0.0138 | 81.4 | 51.0 |

[1]Weight percent of polymer in solution.
[2]Time collecting sample.
[3]The rate at which polymer was produced.
[4]Percent of monomers converted.

TABLE 1b

Copolymerization Reactions of Ethylene and Propylene.

| Run | Wt.[5] G | Catalyst productivity Kg/mole | Mn[6] (×10$^{-3}$) Daltons | PDI[6] |
|---|---|---|---|---|
| 1 | 1931 | 14146 | 102 | 1.63 |
| 2 | 1924.7 | 15038 | 94 | 1.67 |

[5]Grams of polymer solution collected during the time given on column 3 of Table 1a.
[6]Determined by GPC.

I claim:

1. An olefin polymerization catalyst composition which is the reaction product of
    (a) an organometallic transition metal catalyst compound having
        (i) at least one ancillary stabilizing ligand,
        (ii) at least one ligand suitable for insertion of olefins, and
        (iii) a metal-carbon bond capable of scission so as to form an active transition metal cationic center and
    (b) a Group 13 element-containing ionic cocatalyst compound comprising
        (i) a positively charged cation [Ct]$^+$ and
        (ii) a negatively charged anion [A]$^-$,
    said anion comprising a central core Group 13 element to which are bound fluorophenyl ligands, at least one of said fluorophenyl ligands being substituted in the para-position with a siloxy group represented by the symbols —OSiR$_3$, wherein each R is independently a C$_1$–C$_{30}$ hydrocarbyl or hydrocarbylsilyl substituent.

2. The catalyst composition of claim 1 wherein said Group 13 element cocatalyst compound is represented by the formula:

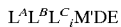
[Ct]$^+$[M(Ar$^f$)$_n$((Ar$^f$)OSiR$_3$)$_{4-n}$]$^-$, where [Ct]$^+$ is a cation capable of abstracting an alkyl group, or breaking a carbon-metal bond, from organometallic compounds containing such, M is boron or aluminum, Ar$^f$ is a fluorophenyl ligand, and each R is a C$_1$–C$_{20}$ hydrocarbyl or hydrocarbylsilyl substituent attached to the Si atom through a secondary or tertiary carbon atom.

3. The catalyst composition of claim 2 wherein each fluorophenyl ligand is perfluorinated.

4. The composition according to claim 1 where [Ct]$^+$ is selected from the group consisting of anilinium and ammonium cations, trityl carbenium cations, Group 11 metal cations, silylium cations, the cations of the hydrated salts of Group 1 or 2 metals, and derivatives of the foregoing anilinium, ammonium, trityl carbenium, and silylium cations containing C$_1$–C$_{20}$ hydrocarbyl, hydrocarbylsilyl, or hydrocarbylamine substituents for one or more hydrogen atoms of said cations.

5. The catalyst composition according to claim 1 wherein said organometallic catalyst compound is a Group 3–10 metal compound capable of activation for olefin polymerization to a monovalent cationic state.

6. The catalyst composition of claim 5 wherein said organometallic catalyst compound is a Group 3–6 metallocene compound having the formula:

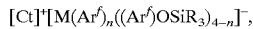
L$^A$L$^B$L$^C_i$M'DE where
    (a) L$^A$ is a substituted or unsubstituted cyclopentadienyl or heterocyclopentadienyl ancillary ligand π-bonded to M';
    (b) L$^B$
        (i) is a substituted or unsubstituted cyclopentadienyl or heterocyclopentadienyl ancillary ligand π-bonded to M'; or
        (ii) is J, a heteroatom ancillary ligand bonded to M';
    wherein L$^A$ and L$^B$ or L$^A$ and J may be covalently bridged together through a Group 13–16 element-containing linking group;
    (c) L$^C_i$ is an optional neutral, non-oxidizing ligand having a dative bond to M' (i equals 0 to 3);
    (d) M' is a Group 3–6 transition metal; and
    (e) D and E are independently labile ligands, each having a metal-carbon bond to M', optionally bridged to each other or to L$^A$ or L$^B$, which metal-carbon bond to M' can be broken for abstraction of D or E by said Group 13 element cocatalyst compound and into which a polymerizable monomer or macromonomer can insert for coordination polymerization.

7. The catalyst composition of claim 6 wherein M' is titanium and L$^B$ is J, a heteroatom ancillary ligand σ-bonded to M'.

8. The catalyst composition of claim 6 wherein M' is zirconium or hafnium and L$^B$ is independently a substituted or unsubstituted cyclopentadienyl or heterocyclopentadienyl ancillary ligand π-bonded to M'.

9. A catalyst for olefin polymerization comprising the reaction product of
    (a) an organometallic transition metal catalyst compound having at least one ancillary, stabilizing ligand and a labile ligand suitable for insertion of olefins and
    (b) an ionic composition comprising a positively charged cation [Ct]$^+$ and a negatively charged anion [A]$^-$, said anion comprising a central core Group 13 element to which are bound fluorophenyl ligands, at least one of said fluorophenyl ligands being substituted in the para-position with a siloxy group represented by the symbol —OSiR$_3$, wherein each R is independently a C$_1$–C$_{30}$ hydrocarbyl or hydrocarbylsilyl substituent.

10. The composition according to claim 9 where [Ct]$^+$ is selected from the group consisting of anilinium and ammonium cations, trityl carbenium cations, Group 11 metal cations, silylium cations, the cations of the hydrated salts of Group 1 or 2 metals, and derivatives of the foregoing anilinium, ammonium, trityl carbenium, and silylium cations containing C$_1$–C$_{20}$ hydrocarbyl, hydrocarbylsilyl, or hydrocarbylamine substituents for one or more hydrogen atoms of said cations.

11. The catalyst composition of claim 10 wherein each fluorophenyl ligand is perfluorinated.

12. A process for the preparation of polyolefins from one or more olefinic monomers comprising combining said olefins under coordination polymerization conditions with an olefin polymerization catalyst composition of one of claims 1–11.

13. The process of claim 12 wherein said Group 13 element cocatalyst complex is represented by the formula:

$$[Ct]^+[M(ArF)_n((ArF)OSiR_3)_{4-n}]^-,$$

where [Ct]$^+$ is cation capable of abstracting an alkyl group, or breaking a carbon-metal bond, from organometallic compounds containing such, M is a Group 13 element, ArF is a fluorinated phenyl group, and each R is a C$_1$–C$_{20}$ hydrocarbyl or hydrocarbylsilyl substituent attached to the Si atom through a secondary or tertiary carbon atom.

14. The process of claim 13 wherein each ArF are perfluorinated phenyl groups.

15. The process of claim 12 wherein said organometallic transition metal catalyst compound is an Group 3–10 transition metal compound capable of activation for olefin polymerization.

16. The process of claim 15 wherein said organometallic catalyst compound is a Group 3–6 metallocene compound having the formula:

$$L^A L^B L^C_i McDE$$

where, L$^A$ is a substituted or unsubstituted cyclopentadienyl or heterocyclopentadienyl ancillary ligand π-bonded to Mc; L$^B$ is a member of the class of ancillary ligands defined for L$^A$, or is J, a heteroatom ancillary ligand bonded to Mc; the L$^A$ and L$^B$ ligands may be covalently bridged together through a Group 13–16 element-containing linking group; L$^C_i$ is an optional neutral, non-oxidizing ligand having a dative bond to Mc (i equals 0 to 3); Mc is a Group 3–6 transition metal; and, D and E are independently labile ligands, each having a metal-carbon bond to M, optionally bridged to each other or to L$^A$ or L$^B$, which bond can be broken for abstraction purposes by said Group 13 element cocatalyst complex and into which a polymerizable monomer or macromonomer can insert for coordination polymerization.

17. The process of claim 16 wherein M is titanium and L$^B$ is J, a heteroatom ancillary ligand σ-bonded to M.

18. The process of claim 16 wherein M is zirconium or hafnium and L$^B$ is independently a substituted or unsubstituted cyclopentadienyl or heterocyclopentadienyl ancillary ligand π-bonded to M.

19. The process of claim 12 wherein said olefin polymerization conditions comprise a solution, supercritical pressure, bulk, slurry or gas phase process conducted at reaction temperatures in a range from 30° C. to 300° C. and pressures from 0 to 2000 bar.

20. The process of claim 19 wherein said process is an adiabatic solution process conducted at a reaction temperature of 40° C. to 250° C.

21. The process of claim 19 wherein said process is bulk, slurry or gas phase, and said activated organometallic complex is carried on or affixed to a particulate support material.

22. The process of claim 19 wherein said olefinic monomers are selected from one or more of the group consisting of ethylene, C$_3$–C$_{20}$ olefins, C$_5$–C$_{20}$ diolefins, C$_7$–C$_{20}$ vinyl aromatic monomers, C$_4$–C$_{20}$ geminally disubstituted olefins and C$_5$–C$_{20}$ cyclic olefins.

23. The catalyst composition according to claim 2 wherein said organometallic catalyst compound is a Group 3–10 metal compound capable of activation for olefin polymerization to a monovalent cationic state.

24. The catalyst composition of claim 23 wherein said organometallic catalyst compound is a Group 3–6 metallocene compound having the formula:

$$L^A L^B L^C_i M'DE$$

where
(a) L$^A$ is a substituted or unsubstituted cyclopentadienyl or heterocyclopentadienyl ancillary ligand π-bonded to M';
(b) L$^B$
  (i) is a substituted or unsubstituted cyclopentadienyl or heterocyclopentadienyl ancillary ligand π-bonded to M'; or
  (ii) is J, a heteroatom ancillary ligand bonded to M';
wherein L$^A$ and L$^B$ or L$^A$ and J may be covalently bridged together through a Group 13–16 element-containing linking group;
(c) L$^C_i$ is an optional neutral, non-oxidizing ligand having a dative bond to M' (i equals 0 to 3);
(d) M' is a Group 3–6 transition metal; and
(e) D and E are independently labile ligands, each having a metal-carbon bond to M', optionally bridged to each other or to L$^A$ or L$^B$, which metal-carbon bond to M' can be broken for abstraction of D or E by said Group 13 element cocatalyst compound and into which a polymerizable monomer or macromonomer can insert for coordination polymerization.

25. The catalyst composition of claim 24 wherein M' is titanium and L$^B$ is J, a heteroatom ancillary ligand σ-bonded to M'.

26. The catalyst composition of claim 24 wherein M' is zirconium or hafnium and L$^B$ is independently a substituted or unsubstituted cyclopentadienyl or heterocyclopentadienyl ancillary ligand π-bonded to M'.

27. The composition according to claim 2 where [Ct]$^+$ is selected from the group consisting of anilinium and ammonium cations, trityl carbenium cations, Group 11 metal cations, silylium cations, the cations of the hydrated salts of Group 1 or 2 metals, and derivatives of the foregoing anilinium, ammonium, trityl carbenium, and silylium cations containing C$_1$–C$_{20}$ hydrocarbyl, hydrocarbylsilyl, or hydrocarbylamine substituents for one or more hydrogen atoms of said cations.

* * * * *